US012788781B2

(12) United States Patent
Wang et al.

(10) Patent No.: US 12,788,781 B2
(45) Date of Patent: Nov. 10, 2026

(54) CELL REPAIR PROTEIN EXTRACT AND PREPARATION METHOD THEREFOR AND USE THEREOF

(71) Applicant: BEIJING DARWIN BIOTECH CO., LTD., Beijing (CN)

(72) Inventors: Yu Wang, Beijing (CN); Wenyong Gao, Beijing (CN); Lin Chen, Beijing (CN); Jianjun Li, Beijing (CN)

(73) Assignee: BEIJING DARWIN BIOTECH CO., LTD., Beijing (CN)

( * ) Notice: Subject to any disclaimer, the term of this patent is extended or adjusted under 35 U.S.C. 154(b) by 206 days.

(21) Appl. No.: 18/833,909

(22) PCT Filed: Jan. 28, 2023

(86) PCT No.: PCT/CN2023/073566
§ 371 (c)(1),
(2) Date: Jul. 28, 2024

(87) PCT Pub. No.: WO2023/143519
PCT Pub. Date: Aug. 3, 2023

(65) Prior Publication Data

US 2025/0195580 A1 Jun. 19, 2025

(30) Foreign Application Priority Data

Jan. 28, 2022 (CN) ........................ 202210105729.X
Apr. 2, 2022 (CN) ......................... 202210351455.2
Jul. 5, 2022 (CN) ......................... 202210793711.3

(51) Int. Cl.

| | |
|---|---|
| ***A61K 35/28*** | (2015.01) |
| ***A61K 38/02*** | (2006.01) |
| ***A61L 27/22*** | (2006.01) |
| ***A61P 17/14*** | (2006.01) |
| ***A61P 19/00*** | (2006.01) |
| ***C07K 1/16*** | (2006.01) |
| ***C12N 5/0775*** | (2010.01) |
| ***C12P 21/00*** | (2006.01) |
| ***C12P 21/06*** | (2006.01) |

(52) U.S. Cl.
CPC .............. *A61K 35/28* (2013.01); *A61K 38/02* (2013.01); *A61L 27/22* (2013.01); *A61P 17/14* (2018.01); *A61P 19/00* (2018.01); *C07K 1/16* (2013.01); *C12N 5/0662* (2013.01); *C12N 5/0668* (2013.01); *C12P 21/00* (2013.01); *C12P 21/06* (2013.01); *A61L 2430/24* (2013.01); *C12N 2500/25* (2013.01); *C12N 2500/32* (2013.01); *C12N 2501/11* (2013.01); *C12N 2501/113* (2013.01); *C12N 2501/115* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 2010/0210530 | A1 | 8/2010 | Naughton |
| 2011/0217385 | A1 | 9/2011 | Lian |
| 2015/0209390 | A1 | 7/2015 | Chu |
| 2019/0201477 | A1 | 7/2019 | Barnea |
| 2020/0038449 | A1 | 2/2020 | Lundgren Åkerlund |

FOREIGN PATENT DOCUMENTS

| | | | |
|---|---|---|---|
| CN | 101591644 | A | 12/2009 |
| CN | 101810855 | A | 8/2010 |
| CN | 102827807 | A | 12/2012 |
| CN | 103555665 | A | 2/2014 |
| CN | 103784474 | A | 5/2014 |
| CN | 108126187 | A | 6/2018 |
| CN | 108865986 | A | 11/2018 |
| CN | 110227057 | A | 9/2019 |
| CN | 110269833 | A | 9/2019 |

(Continued)

OTHER PUBLICATIONS

Nishikawa et al. "Filtrated Adipose Tissue-Derived Mesenchymal Stem Cell Lysate Ameliorates Experimental Acute Colitis in Mice" (published on-line Jun. 2020) Digestive Diseases Sci, vol. 66: 1034-1044. (Year: 2021).*

Caplan & Correa "The MSC: An Injury Drugstore" (2011), Cell Stem Cell, vol. 9: 11-15. (Year: 2011).*

The first search report of counterpart foreign application No. CN202310042914.3 issued on May 13, 2024.

Li, Xian-song; et al. Chinese Journal of Tissue Engineering Research. Feb. 5, 2014 vol. 18, No. 6. Bone marrow mesenchymal stem cells for epidermal and skin appendage regeneration. ISSN 2095-4344 CN 21-1581/R CODEN: ZLKHAH. p. 853-859.

Aonnicha Sombatsri; et al. Archives of Pharmacal Research, vol. 41, No. 4 . Mar. 15, 2018○ New limonophyllines A-C from the stem of Atalantia monophylla and cytotoxicity against cholangiocarcinoma and HepG2 cell lines. p. 431-437.

(Continued)

*Primary Examiner* — Teresa E Knight
(74) *Attorney, Agent, or Firm* — The Sun IP Law

(57) ABSTRACT

The present disclosure relates to a cell protein extract having cell repair effect. The preparation thereof includes the following steps: (1) placing mesenchymal passage cells with a density of $1.0\times10^6$ cells/mL to $5.0\times10^7$ cells/mL in a culture medium containing DMEM/F12 40-50%, RPMI1640 40-50%, bovine serum albumin (BSA) 0.1-2%, epidermal growth factor (EGF) 1-15 μg/mL, fibroblast growth factor (FGF) 1-15 μg/mL, insulin transferrin 1-15 μg/mL, compound amino acids (18AA) 0.01-0.1%, and 2-10 μmol/L of a stressor, and then culturing the cells under conditions of 37.0° C.±0.5° C. and 5%±1.0% $CO_2$ for 10 minutes to 14 hours, and then performing isolation, washing, and collecting cells, wherein the stressor is selected from any one of compounds 1-16 or a combination thereof; (2) performing an ultrasonic treatment on the collected cells at 2° C.-8° C. to prepare a cell lysate, and filtering same so as to obtain the cell protein extract.

20 Claims, 4 Drawing Sheets

(56) References Cited

FOREIGN PATENT DOCUMENTS

| | | | |
|---|---|---|---|
| CN | 110507597 | A | 11/2019 |
| CN | 111233972 | A | 6/2020 |
| CN | 111334473 | A | 6/2020 |
| CN | 111375087 | A | 7/2020 |
| CN | 111821250 | A | 10/2020 |
| CN | 111840330 | A | 10/2020 |
| CN | 112569343 | A | 3/2021 |
| CN | 113462673 | A | 10/2021 |
| CN | 113509431 | A | 10/2021 |
| CN | 113750116 | A | 12/2021 |
| CN | 113893266 | A | 1/2022 |
| CN | 116555174 | A | 8/2023 |
| CN | 116555175 | A | 8/2023 |
| CN | 116555176 | A | 8/2023 |
| IN | 201941047662 | A | 11/2019 |

OTHER PUBLICATIONS

Alasdair G. Kay; et al. Scientific Reports, vol. 113.Dec. 21, 2017. Mesenchymal Stem Cell-Conditioned Medium Reduces Disease Severity and Immune Responses in Inflammatory Arthritis. Abstract, p. 8, paragraph 4.
The first search report of counterpart foreign application No. CN202310042913.9 issued on Jan. 15, 2024.
The grant supplementary search report of counterpart foreign application No. CN202310042914.3 issued on Sep. 3, 2024.
The first search report of counterpart foreign application No. CN202310042911.X issued on Jun. 17, 2024.
The grant supplementary search report of counterpart foreign application No. CN202310042911.X issued on Jul. 18, 2024.
The first search report of counterpart foreign application No. CN202310042910.5 issued on Nov. 12, 2024.
The grant supplementary search report of counterpart foreign application No. CN202310042910.5 issued on Mar. 17, 2025.
The first office action of counterpart foreign application No. JP2024-544824 issued on Oct. 10, 20205.
Aonnicha Sombatsri et al. "New limonophyllines A-C from the stem of Atalantia monophylla and cytotoxicity against cholangiocarcinoma and HepG2 cell lines." Arch Pharm Res. vol. 41, No. 4, Mar. 15, 2018. See abstract and Figure 1.
The search report of counterpart PCT application No. PCT/CN2023/073582 issued on May 6, 2023.
The search report of counterpart PCT application No. PCT/CN2023/073590 issued on Apr. 30, 2023.
The search report of counterpart PCT application No. PCT/CN2023/073566 issued on Mar. 4, 2023.
Han, Junzhu, et al. "Comparison of chondrogenic differentiation potential of three types of mesenchymal stem cells." Modern Advances in Biomedicine, vol. 19, No. 12, Dec 31, 2019 (Dec. 31, 2019), full text, especially sections 1.2.3, Table 1, and Abstract.

* cited by examiner

CELL REPAIR PROTEIN EXTRACT AND PREPARATION METHOD THEREFOR AND USE THEREOF

TECHNICAL FIELD

The present disclosure belongs to the field of biopharmaceutical technology and specifically relates to a cell repair protein extract and its preparation method therefore and use thereof.

BACKGROUND

Cells are the basic units of life activities and the basis of the health of the body. When the redox balance of the body is disrupted, it can cause an interruption in redox signaling and control, which will cause oxidative stress damage and lead to a variety of diseases. Timely repair of damaged cells can significantly improve and treat related diseases.

When cells and microorganisms are subjected to external stimuli and external stressors (including cold, heat, acid, alkali, current, radiation, chemicals, etc.), they will be induced to produce stress proteins due to stress responses. Reference 1 (New limonophyllines A-C from the stem of *Atalantia monophylla* and cytotoxicity against cholangiocarcinoma and HepG2 cell lines, Arch. Pharm. Res. (2018) 41:431-437) reveals that compounds 1-16 extracted from the *Rutaceae* plant (*Atalantia monophylla*) exhibiting activities such as inhibiting tumor cell growth.

Mesenchymal stem cells (MSCs) have the potential of self-replication and multi-lineage differentiation. They are widely found in bone marrow, fat, synovial membrane, dental pulp, amniotic fluid, placenta, umbilical cord, embryo, umbilical cord blood, amniotic membrane, peripheral blood, muscle, urine and other tissues. Mesenchymal stem cells (MSCS) have the characteristics of wide sources, no need for matching, low infection rate, strong differentiation potential, strong proliferation ability, and easy collection. They can produce active factors such as stem cell growth factor (SCF), nerve growth factor (NGF), interleukin-6 (IL-6), interleukin-7 (IL-7), tumor necrosis factor (TNF), interferon (IFN), which involve in the regulation of cell growth, cell apoptosis, cell differentiation, antiviral, immune maturation and other processes, and are used in immune regulation, tissue repair and treatment of acute lung injury, severe pneumonia, acute respiratory distress syndrome and other diseases. However, MSCs products need to be refrigerated during production, storage, transportation and application, and their cell viability remains ≤12 h, which limits their therapeutic application. Therefore, it is necessary to develop safe and effective skin repair drugs to meet clinical needs.

SUMMARY

The purpose of the present disclosure is to provide a cell protein extract having cell repair effect, the preparation thereof includes the following steps:

(1) placing mesenchymal passage cells with a density of $1.0\times10^6$ cells/mL to $5.0\times10^7$ cells/mL in a culture medium containing DMEM/F12 40-50%, RPMI1640 40-50%, bovine serum albumin (BSA) 0.1-2%, epidermal growth factor (EGF) 1-15 μg/mL, fibroblast growth factor (FGF) 1-15 μg/mL, insulin transferrin 1-15 μg/mL, compound amino acids (18AA) 0.01-0.1%, and 2-10 μmol/L of a stressor, and then culture it under conditions of 37.0° C.±0.5° C. and 5%±1.0% $CO_2$ for 10 minutes to 14 hours, and then performing isolation, washing, and collecting cells, wherein the stressor is selected from any one of compounds 1-16 or a combination thereof;

| compound | General formula | Substituents |
|---|---|---|
| 1 | 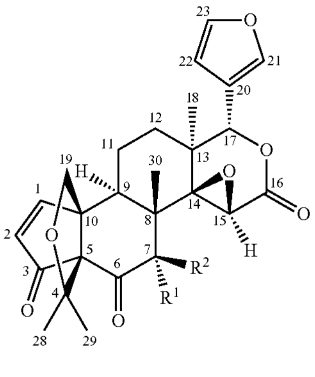 | $R^1 = OCH_3$, $R^2 = OH$ |
| 2 | | $R^1 = R^2 = OH$ |
| 3 | | $R^1 = OH$, $R^2 = H$ |

-continued
| compound | General formula | Substituents |
|---|---|---|
| 4 | 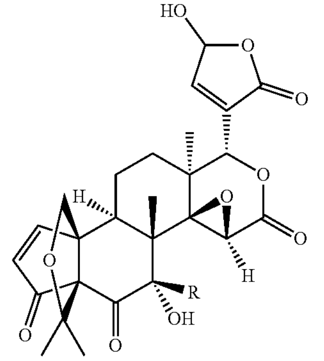 | R = H |
| 5 | | R = OH |
| 6 | 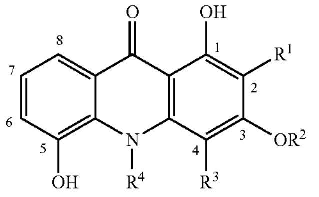 | $R^1$ = prenyl, $R^2$ = H, $R^3$ = prenyl, $R^4$ = $CH_3$ |
| 7 | | $R^1$ = prenyl, $R^2$ = H, $R^3$ = prenyl, $R^4$ = H |
| 8 | | $R^1$ = H, $R^2$ = H, $R^3$ = $OCH_3$, $R^4$ = $CH_3$ |
| 9 | | $R^1$ = H, $R^2$ = $CH_3$, $R^3$ = $OCH_3$, $R^4$ = $CH_3$ |
| 10 | | $R^1$ = $OCH_3$, $R^2$ = H, $R^3$ = H, $R^4$ = $CH_3$ |
| 11 | | $R^1$ = $OCH_3$, $R^2$ = H, $R^3$ = $OCH_3$, $R^4$ = $CH_3$ |
| 12 | | $R^1$ = prenyl, $R^2$ = $CH_3$, $R^3$ = H, $R^4$ = H |
| 13 | 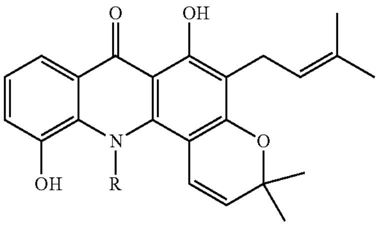 | R = H |
| 14 | | R = $CH_3$ |
| 15 | 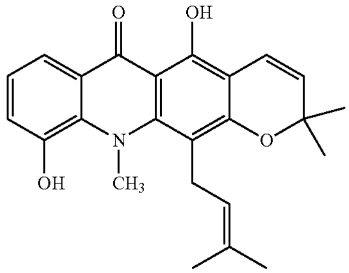 [SMILES: CC(C)=CCc1c2c(c(O)c3c(=O)c4cccc(O)c4n(C)c13)C=CC(C)(C)O2] | |
| 16 | 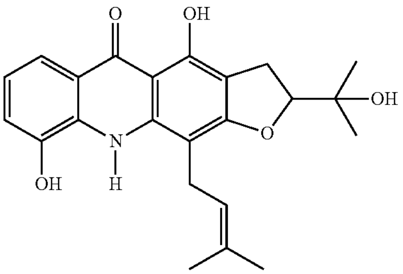 [SMILES: CC(C)=CCc1c2c(c(O)c3c(=O)c4cccc(O)c4[nH]c13)CC(C(C)(C)O)O2] | |

(2) dispersing the collected cells in a solvent at a density of $5.0\times10^6$ cells/mL-$1.0\times10^7$ cells/mL, and then performing an ultrasonic treatment on the collected cells at 2° C.-8° C. to prepare a cell lysate, wherein, the solvent is selected from any one or a combination of physiological saline, 5% glucose solution, phosphate buffer solution (PBS), TBPS buffer, TBST buffer, or Tris buffer;

(3) separating the cell lysis solution prepared in step (2), then sequentially filtering a separated solution through 0.45 m and 0.22 m filter membranes, thereby obtaining the cell protein extract.

In a preferred technical solution of the present disclosure, the culture medium of step (1) contains DMEM/F12 42-45%, RPMI1640 42-45%, bovine serum albumin (BSA) 0.5-1.5%, epidermal growth factor (EGF) 5-10 μg/mL, fibroblast growth factor (FGF) 5-10 μg/mL, insulin transferrin 5-10 μg/mL, compound amino acids (18AA) 0.02-0.05%, and 3-8 μmol/L of stressors.

In a preferred technical solution of the present disclosure, the culture medium of step (1) contains DMEM/F12 45%, RPMI1640 45%, bovine serum albumin (BSA) 0.5%, epidermal growth factor (EGF) 10 μg/mL, fibroblast growth factor (FGF) 10 μg/mL, insulin transferrin 10 μg/mL, compound amino acids (18AA) 0.05%, and 4-6 μmol/L of stressors.

In a preferred technical solution of the present disclosure, the density of mesenchymal passage cells in step (1) is $2.0\times10^6$-$2.0\times10^7$ cells/mL, preferably $5.0\times10^6$-$1.0\times10^7$ cells/mL.

In a preferred technical solution of the present disclosure, the mesenchymal passage cells in step (1) are cultured in a culture medium for 30 minutes to 13 hours, preferably 45 minutes to 12 hours.

In a preferred technical solution of the present disclosure, the solvent for washing cells in step (1) is selected from any one or a combination of physiological saline, 5% glucose solution, phosphate buffer (PBS), TBPS buffer, TBST buffer, Tris buffer, with a washing frequency of 2-5 times, preferably 3-4 times.

In a preferred technical solution of the present disclosure, the isolation in step (1) is selected from centrifugation and filtration or a combination thereof, wherein the centrifugation condition is 1000-2000 rpm*3-15 min, preferably 1200 rpm~1500 rpm*5-10 min.

In a preferred technical solution of the present disclosure, the conditions of ultrasonic treatment of step (2) are as follows: operating at 2° C.-8° C., 25 kHZ, 360 W for 3 seconds with a gap of 1 second, and performing ultrasonic treatment for 1-5 minutes.

In a preferred technical solution of the present disclosure, the separation in step (3) is selected from 2000-8000 rpm*10-30 min centrifugation, multi-stage centrifugation, multi-stage filtration or a combination thereof, preferably 3000-7000 rpm*15-25 min.

In a preferred technical solution of the present disclosure, the multi-stage centrifugation in step (3) is sequentially 3000-4000 rpm*3-5 minutes, 5000-6000 rpm*3-5 minutes, and 7000 rpm*5-8 minutes.

In a preferred technical solution of the present disclosure, the pore size of the multi-stage filtration membrane is selected from any one of 80 μm, 50 μm, 30 μm, 10 μm, or 5 μm.

In a preferred technical solution of the present disclosure, the protein extract prepared in step (3) is frozen, preferably stored at −40° C. to −20° C.

In a preferred technical solution of the present disclosure, a freeze-dried protectant is added to the filtrate collected in step (3) to produce a freeze-dried preparation. The freeze-dried protectant is selected from any one or a combination of mannitol, sorbitol, dextran, glycerol, sucrose, trehalose, glucose, lactose, maltose, glucan, glycerol trioctanoate (HES), polyethylene glycol, ethylene glycol, phosphate, acetate, citrate, sorbitol or starch.

In a preferred technical solution of the present disclosure, the freeze-dried preparation contains a freeze-dried protectant of 0.7-7% by a mass percentage, preferably 1-5%.

In a preferred technical solution of the present disclosure, a protein stabilizer is optionally added to the filtrate collected in step (3), wherein the protein stabilizer is selected from any one of albumin, zinc salt, or aluminum salt.

In a preferred technical solution of the present disclosure, the freeze-dried preparation has a pH of 6-8, preferably a pH of 7-7.5.

In a preferred technical solution of the present disclosure, the freeze-dried preparation is remelted with an isotonic solution before use, and then used in any one or a combination of application, rolling needle, microneedle, massage, intravenous injection, intramuscular injection, subcutaneous injection, acupoint injection, or lumbar puncture. The isotonic solution is selected from any one or a combination of physiological saline, 5% glucose solution, phosphate buffer (PBS), TBPS buffer, TBST buffer, or Tris buffer.

In a preferred technical solution of the present disclosure, the cultivation of mesenchymal stem cells or primary mesenchymal stem cells adopts the cultivation method in the field.

In a preferred technical solution of the present disclosure, the cultivation of mesenchymal stem cells includes the following steps: adding primary mesenchymal stem cells to a passaging medium with an initial density of $5.0\times10^5$-$5.0\times10^6$ cells/ml, and then culturing them under conditions of 37.0° C.±0.5° C. and 5%±1.0% $CO_2$ for 10-15 days. Every 2-3 days, after observing the yellowing of the passaging medium, half of the passaging medium is replaced, wherein the passaging medium contains DMEM/F12 medium containing 10% FBS, 100 U/ml penicillin, and 100 g/ml streptomycin.

In a preferred technical solution of the present disclosure, the cultivation of primary mesenchymal stem cells includes the following steps:

1) cleaning and disinfecting an umbilical cord, dissecting the tissue, taking the Wharton's Jelly, cutting it into 3 $mm^3$ small pieces, centrifuging, cleaning, collecting tissue blocks, placing them in DMEM/F12 medium containing 10% fetal bovine serum FBS, 100 μg/ml penicillin, and 100 μg/ml streptomycin, and then culturing them under conditions of 37.0° C.±0.5° C. and 5%±1.0% $CO_2$, replacing half of the medium every 2-3 days and culturing until cells growing out from the tissue blocks;

2) shaking and collecting low-layer cells, washing with PBS, adding 0.25% trypsin for digestion for 2-3 minutes, adding an equal volume of trypsin termination solution to stop digestion, gently blowing with a straw, centrifuging at 1200-1500 rpm/min*5-8 minutes, and collecting the cells.

The purpose of the present disclosure is to provide a preparation method for a cell protein extract having cell repair efficacy, including the following steps:

(1) placing mesenchymal passage cells with a density of $1.0\times10^6$ cells/mL to $5.0\times10^7$ cells/mL in a culture medium containing DMEM/F12 40-50%, RPMI1640

40-50%, bovine serum albumin (BSA) 0.1-2%, epidermal growth factor (EGF) 1-15 μg/mL, fibroblast growth factor (FGF) 1-15 μg/mL, insulin transferrin 1-15 μg/mL, compound amino acids (18AA) 0.01-0.1%, and 2-10 μmol/L of a stressor, and then culturing the cells under conditions of 37.0° C.±0.5° C. and 5%±1.0% $CO_2$ for 10 minutes to 14 hours, and then performing isolation, washing, and collecting cells, wherein the stressor is selected from any one of compounds 1-16 or a combination thereof;

(2) dispersing the collected cells in a solvent at a density of $5.0\times10^6$ cells/mL-$1.0\times10^7$ cells/mL, and then performing an ultrasonic treatment on the collected cells at 2° C.-8° C. to prepare a cell lysate, wherein, the solvent is selected from any one or combination of physiological saline, 5% glucose solution, phosphate buffer solution (PBS), TBPS buffer, TBST buffer, or Tris buffer;

(3) separating the cell lysis solution prepared in step (2), then sequentially filtering a separated solution through 0.45 μm and 0.22 μm filter membranes, thereby obtaining the cell protein extract.

In a preferred technical solution of the present disclosure, the culture medium in step (1) contains DMEM/F12 42-45%, RPMI1640 42-45%, bovine serum albumin (BSA) 0.5-1.5%, epidermal growth factor (EGF) 5-10 μg/mL, fibroblast growth factor (FGF) 5-10 μg/mL, insulin transferrin 5-10 μg/mL, compound amino acids (18AA) 0.02-0.05%, and 3-8 μmol/L of the stressor.

In a preferred technical solution of the present disclosure, the culture medium in step (1) contains DMEM/F12 45%, RPMI1640 45%, bovine serum albumin (BSA) 0.5%, epidermal growth factor (EGF) 10 μg/mL, fibroblast growth factor (FGF) 10 μg/mL, insulin transferrin 10 μg/mL, compound amino acids (18AA) 0.05%, and 4-6 μmol/L of the stressor.

In a preferred technical solution of the present disclosure, the density of mesenchymal passage cells in step (1) is $2.0\times10^6$-$2.0\times10^7$ cells/mL, preferably $5.0\times10^6$-$1.0\times10^7$ cells/mL.

In a preferred technical solution of the present disclosure, the mesenchymal passage cells in step (1) are cultured in a culture medium for 30 minutes to 13 hours, preferably 45 minutes to 12 hours.

In a preferred technical solution of the present disclosure, the solvent for washing cells in step (1) is selected from any one or a combination of physiological saline, 5% glucose solution, phosphate buffer (PBS), TBPS buffer, TBST buffer, Tris buffer, with a washing frequency of 2-5 times, preferably 3-4 times.

In a preferred technical solution of the present disclosure, the isolation in step (1) is selected from centrifugation and filtration or a combination thereof, wherein the centrifugation condition is 1000-2000 rpm*3-15 min, preferably 1200 rpm~1500 rpm*5-10 min.

In a preferred technical solution of the present disclosure, the cultivation of mesenchymal stem cells or primary mesenchymal stem cells adopts the cultivation method in the field.

In a preferred technical solution of the present disclosure, the cultivation of mesenchymal stem cells includes the following steps: adding primary mesenchymal stem cells to a passaging medium with an initial density of $5.0\times10^5$-$5.0\times10^6$ cells/ml, and then culturing them under conditions of 37.0° C.±0.5° C. and 5%±1.0% $CO_2$ for 10-15 days. Every 2-3 days, after observing the yellowing of the passaging medium, half of the passaging medium is replaced, wherein the passaging medium contains DMEM/F12 medium containing 10% FBS, 100 U/ml penicillin, and 100 μg/ml streptomycin.

In a preferred technical solution of the present disclosure, the cultivation of primary mesenchymal stem cells includes the following steps:

1) cleaning and disinfecting an umbilical cord, dissecting the tissue, taking the Wharton's Jelly, cutting it into 3 $mm^3$ small pieces, centrifuging, cleaning, collecting tissue blocks, placing them in DMEM/F12 medium containing 10% fetal bovine serum FBS, 100 μg/ml penicillin, and 100 μg/ml streptomycin, and then culturing them under conditions of 37.0° C.±0.5° C. and 5%±1.0% $CO_2$, replacing half of the medium every 2-3 days until cells growing out from tissue blocks;

2) shaking and collecting low-layer cells, washing with PBS, adding 0.25% trypsin for digestion for 2-3 minutes, adding an equal volume of trypsin termination solution to stop digestion, gently blowing with a straw, centrifuging at 1200-1500 rpm/min*5-8 minutes, and collecting the cells.

In a preferred technical solution of the present disclosure, the conditions of ultrasonic treatment of step (2) are as follows: operating at 2° C.-8° C., 25 kHZ, 360 W for 3 seconds with a gap of 1 second, and performing ultrasonic treatment for 1-5 minutes.

In a preferred technical solution of the present disclosure, the separation in step (3) is selected from 2000-8000 rpm*10-30 min centrifugation, multi-stage centrifugation, and multi-stage filtration or a combination thereof, preferably 3000-7000 rpm*15-25 min.

In a preferred technical solution of the present disclosure, the multi-stage centrifugation in step (3) is sequentially 3000-4000 rpm*3-5 minutes, 5000-6000 rpm*3-5 minutes, and 7000 rpm*5-8 minutes.

In a preferred technical solution of the present disclosure, the pore size of the multi-stage filtration membrane is selected from any one of 80 μm, 50 μm, 30 μm, 10 μm, or 5 μm.

In a preferred technical solution of the present disclosure, the protein extract prepared in step (3) is frozen, preferably stored at −40° C. to −20° C.

In a preferred technical solution of the present disclosure, a freeze-dried protectant is added to the filtrate collected in step (3) to produce a freeze-dried preparation, which is obtained by freeze-drying. The freeze-dried protectant is selected from any one or a combination of mannitol, sorbitol, dextran, glycerol, sucrose, trehalose, glucose, lactose, maltose, glucan, glycerol trioctanoate (HES), polyethylene glycol, ethylene glycol, phosphate, acetate, citrate, sorbitol, or starch.

In a preferred technical solution of the present disclosure, the freeze-dried preparation contains a freeze-dried protectant of 0.7-7% by a mass percentage, preferably 1-5%.

In a preferred technical solution of the present disclosure, a protein stabilizer is optionally added to the filtrate collected in step (3), wherein the protein stabilizer is selected from any one of albumin, zinc salt, or aluminum salt.

In a preferred technical solution of the present disclosure, the freeze-dried preparation has a pH of 6-8, preferably a pH of 7-7.5.

In a preferred technical solution of the present disclosure, the freeze-dried preparation is remelted with an isotonic solution before use, and then used in any one or a combination of application, rolling needle, microneedle, massage, intravenous injection, intramuscular injection, subcutaneous injection, acupoint injection, or lumbar puncture. The isotonic solution is selected from any one or a combination of physiological saline, 5% glucose solution, phosphate buffer (PBS), TBPS buffer, TBST buffer, or Tris buffer.

Another object of the present disclosure is to provide a cell repair composition containing a cell protein extract having cell repair efficacy and a pharmaceutically acceptable carrier according to the present disclosure.

The pharmaceutically acceptable dosage or type of carrier of the present disclosure depends on factors such as the physicochemical properties and content of the active ingredients in the composition, formulation type, dissolution and bioavailability of the formulation.

The composition of the present disclosure can be various dosage forms in the field, and can be prepared using formulation techniques in the field.

In a preferred technical scheme of the disclosure, the composition is selected from any kind of freeze-dried preparation, gel, nasal spray, paste, cream, emulsion, liquid dressing, injection and suppository.

In a preferred technical solution of the present disclosure, the administration method of the combination is selected from any one or a combination of application, rolling needle, microneedle, massage, intravenous injection, muscle injection, subcutaneous injection, acupoint injection or lumbar puncture.

Another object of the present disclosure is to provide a cell protein extract or its composition having cell repair efficacy for the preparation of medication or product for cell repair, joint repair, cartilage repair, cell repair of skin injury, cell repair of nerve damage, repair of organ damage, repair of pulmonary fibrosis, repair of liver damage, repair of kidney damage, ovarian repair, anti-Crohn's disease, anti-sub health, or anti-aging.

Another object of the present disclosure is to provide compounds 1-16 for the use of stress induced stem cell production of functional proteins with repair effects.

In a preferred technical solution of the present disclosure, the repair is any one of cell repair, hair follicle repair, joint repair, or nerve repair.

Unless otherwise specified, when the present disclosure relates to the percentage between liquids, the said percentage is volume/volume percentage; when the present disclosure relates to the percentage between liquid and solid, the percentage is the volume/weight percentage; When the present disclosure relates to the percentage between solid and liquid, the percentage is the weight/volume percentage; The rest are weight/weight percentage.

Unless otherwise specified, the present disclosure adopts the following methods for detection:

1. Identification of mesenchymal stem cells by MSCs: "Standards for the culture and quality control of umbilical cord mesenchymal stromal cells for neurorestorative clinical application".
2. Use commercially available reagent kits to detect levels of reactive oxygen species (IOD), superoxide dismutase SOD, and malondialdehyde MDA.

Compared with prior art, the present disclosure has the following beneficial effects:

1. The present disclosure scientifically screened a culture medium containing stressors to induce mesenchymal stem cells to produce cell proteins having cell repair effects. The obtained cell protein extract has the advantages of repairing nerve damage, repairing joint damage, repairing damaged hair follicle cells, repairing skin damage, repairing pulmonary fibrosis, repairing liver damage, repairing kidney damage, repairing sub-health, repairing premature ovarian failure, preventing and treating Crohn's disease, anti-aging, etc., and has high purity, good stability, safety and effectiveness. It effectively solves the need for refrigeration for live cells and its activity is limited by cell viability time.
2. The preparation method of the present disclosure has the advantages of simple operation, green environmental protection, lower cost, and suitability for industrial production.

DETAILED DESCRIPTION OF THE EMBODIMENTS

Figure 1:
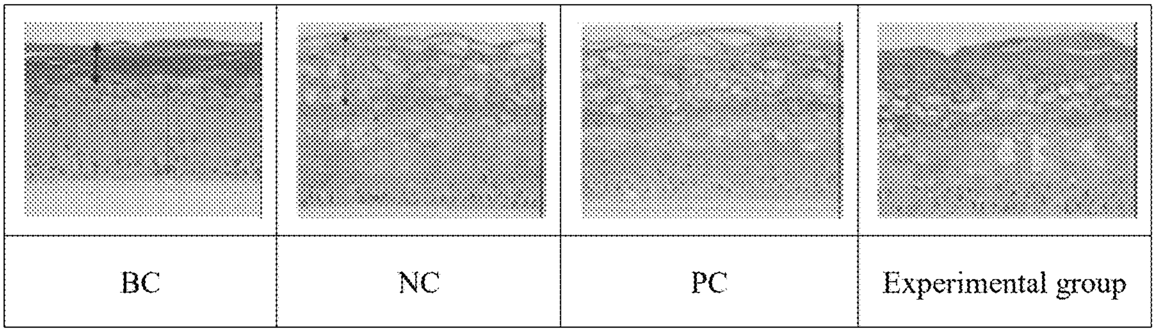
FIG. 1. Study on the repair effect of the cell protein extract of the present disclosure on oxidative damaged skin.

The following will further explain and describe the detailed content of the present disclosure in conjunction with specific embodiments, but this does not limit the scope of protection of the present disclosure.

1. Culture of Primary Mesenchymal Stem Cells

The cultivation of primary mesenchymal stem cells includes the following steps:

1) after cleaning and disinfecting the umbilical cord, dissecting the tissue, taking the Wharton's Jelly, cutting it into 3 $mm^3$ small pieces, centrifuging, cleaning, collecting tissue blocks, placing them in a culture bottle, adding DMEM/F12 culture medium containing 10% fetal bovine serum FBS, 100 μg/ml penicillin, and 100 μg/ml streptomycin, and then culturing it under 37° C. and 5% $CO_2$ conditions to promote its adhesion. Every 2-3 days, observing the yellowing of the culture medium, replacing half of the culture medium, and culturing for 10-12 days until cells can be seen climbing out at the edge of the tissue blocks;
2) gently shaking to make the tissue blocks fall off, collecting the tissue block and lower layer cells separately, and then attaching the collected tissue blocks to the wall for culture;

3) after cleaning the collected low-layer cells with PBS, adding an appropriate amount of 0.25% trypsin and digesting for 2-3 minutes, adding an equal volume of trypsin termination solution to stop digestion. Gently blowing the bottom of the bottle with a straw, centrifuging at 1500 rpm/min*5 minutes, and collecting the cells.

2. Passage Culture of Primary Mesenchymal Stem Cells

Passage culture of primary mesenchymal stem cells: primary mesenchymal stem cells were added to DMEM/F12 medium containing 10% FBS, 100 U/ml penicillin, and 100 μg/ml streptomycin at an initial density of $1.0\times10^5$-$6.0\times10^6$ cells/ml, and then cultured under conditions of 37.0° C.±0.5° C. and 5%±1.0% $CO_2$ for 10-15 days, with intervals of 2-3 days. After observing the yellowing of the medium, half of the medium was replaced.

3. Reference 1 for the preparation of compounds 1-16 (New limonophyllines A-C from the stem of *Atalantia monophylla* and cytotoxicity against cholangiocarcinoma and HepG2 cell lines, Arch. Pharm. Res. (2018) 41:431-437).

Example 1 Preparation of Cell Protein Extract of the Present Disclosure

The preparation method of the cell protein extract of the present disclosure included the following steps:

(1) Adding mesenchymal passage cells with a density of $5.0\times10^6$ cells/mL to the culture medium containing DMEM/F12 45%, RPMI1640 45%, bovine serum albumin (BSA) 0.5%, epidermal growth factor (EGF) 10 μg/mL, fibroblast growth factor (FGF) 10 μg/mL, insulin transferrin 10 μg/mL, compound amino acids (18AA) 0.05% and compound 16 with 5 μmol/L; then, incubating it at 37° C. and 5% $CO_2$ for 30 minutes, then centrifuging it at 1200 rpm*5 minutes, washing it with PBS three times, and collecting the cells;

(2) dispersing the collected cells in step (1) into physiological saline at a density of $8.0\times10^6$ cells/mL, and performing an ultrasonic treatment on the collected cells for 3 seconds with a gap of 1 second under conditions of 2-8° C., 25 kHz, and 360 W for 2 minutes to prepare a cell lysis solution;

(3) centrifuging the cell lysis solution prepared in step (2) at 7000 rpm*20 minutes, and filtering the obtained solution through 0.45 m and 0.22 m filter membranes sequentially to obtain the desired solution.

Example 2 Preparation of Freeze-Dried Cell Protein Extract Preparation of the Present Disclosure Adding the required amount of mannitol to the cell protein extract prepared in Example 1, stirring, mixing well, and freezing dry. The resulting freeze-dried preparation contained 2% mannitol (m/m).

Example 3 Preparation of Cell Protein Extract of the Present Disclosure

The preparation method of the cell protein extract of the present disclosure included the following steps:

(1) Adding mesenchymal passage cells with a density of $8.0\times10^6$ cells/mL to the culture medium containing DMEM/F12 45%, RPMI1640 45%, bovine serum albumin (BSA) 0.5%, epidermal growth factor (EGF) 10 μg/mL, fibroblast growth factor (FGF) 10 μg/mL, insulin transferrin 10 μg/mL, compound amino acids (18AA) 0.05% and compound 16 with 5 μmol/L; then incubating it at 37° C. and 5% $CO_2$ for 4 hours, then centrifuging it at 1200 rpm*5 minutes, washing it with PBS three times, and collecting the cells;

(2) dispersing the collected cells in step (1) into physiological saline at a density of $1.0\times10^7$ cells/mL, and performing an ultrasonic treatment on the collected cells for 3 seconds with a gap of 1 second under conditions of 2-8° C., 25 kHz, and 360 W for 2 minutes to prepare a cell lysis solution;

(3) centrifuging the cell lysis solution prepared in step (2) at 7000 rpm*20 minutes, and filtering the obtained solution through 0.45 μm and 0.22 μm filter membranes sequentially to obtain the desired solution.

Example 4 Preparation of Freeze-Dried Cell Protein Extract Preparation of the Present Disclosure Adding the required amount of mannitol to the cell protein extract prepared in Example 3, stirring, mixing well, and freezing dry. The resulting freeze-dried preparation contained 5% mannitol (m/m).

Example 5 Preparation of Cell Protein Extract of the Present Disclosure

The preparation method of the cell protein extract of the present disclosure included the following steps:

(1) Adding mesenchymal passage cells with a density of $5.0\times10^6$ cells/mL to the culture medium containing DMEM/F12 45%, RPMI1640 45%, bovine serum albumin (BSA) 0.5%, epidermal growth factor (EGF) 10 μg/mL, fibroblast growth factor (FGF) 10 μg/mL, insulin transferrin 10 μg/mL, compound amino acids (18AA) 0.05% and compound 16 with 5 μmol/L; then incubating it at 37° C. and 5% $CO_2$ for 12 hours, then centrifuging it at 1200 rpm*5 minutes, washing it with PBS three times, and collecting the cells;

(2) dispersing the collected cells in step (1) into physiological saline at a density of $1.0\times10^7$ cells/mL, and performing an ultrasonic treatment on the collected cells for 3 seconds with a gap of 1 second under conditions of 2-8° C., 25 kHz, and 360 W for 2 minutes to prepare a cell lysis solution;

(3) centrifuging the cell lysis solution prepared in step (2) at 7000 rpm*20 minutes, and filtering the obtained solution through 0.45 μm and 0.22 μm filter membranes sequentially to obtain the desired solution.

Example 6 Preparation of Freeze-Dried Cell Protein Extract Preparation of the Present Disclosure Adding the required amount of mannitol to the cell protein extract prepared in Example 5, stirring, mixing well, and freezing dry. The resulting freeze-dried preparation contained 2% mannitol (m/m).

Example 7 Preparation of Cell Protein Extract of the Present Disclosure

The preparation method of the cell protein extract of the present disclosure included the following steps:

(1) Adding mesenchymal passage cells with a density of $5.0\times10^6$ cells/mL to the culture medium containing DMEM/F12 45%, RPMI1640 45%, bovine serum albumin (BSA) 0.5%, epidermal growth factor (EGF) 10 μg/mL, fibroblast growth factor (FGF) 10 μg/mL, insulin transferrin 10 μg/mL, compound amino acids (18AA) 0.05% and compound 13 with 5 μmol/L; then incubating it at 37° C. and 5% $CO_2$ for 30 minutes, then centrifuging it at 1200 rpm*5 minutes, washing it with PBS three times, and collecting the cells;

(2) dispersing the collected cells in step (1) into physiological saline at a density of $7.0\times10^6$ cells/mL, and performing an ultrasonic treatment on the collected cells for 3 seconds with a gap of 1 second under conditions of 2-8° C., 25 kHz, and 360 W for 2 minutes to prepare a cell lysis solution;

(3) centrifuging the cell lysis solution prepared in step (2) at 7000 rpm*20 minutes, and filtering the obtained solution through 0.45 m and 0.22 m filter membranes sequentially to obtain the desired solution. The prepared cell protein extract can be freeze-dried as needed.

Example 8 Preparation of Freeze-Dried Cell Protein Extract Preparation of the Present Disclosure Adding sorbitol to the cell protein extract prepared in Example 7, stirring well, mixing well, and freezing dry. The resulting freeze-dried preparation contained 3% sorbitol (m/m).

Example 9 Preparation of Cell Protein Extract of the Present Disclosure

The preparation method of the cell protein extract of the present disclosure included the following steps:

(1) Adding mesenchymal passage cells with a density of $1.0\times10^7$ cells/mL to the culture medium containing DMEM/F12 45%, RPMI1640 45%, bovine serum albumin (BSA) 0.5%, epidermal growth factor (EGF) 10 μg/mL, fibroblast growth factor (FGF) 10 μg/mL, insulin transferrin 10 μg/mL, compound amino acids (18AA) 0.05% and compound 14 with 8 μmol/L; then incubating it at 37° C. and 5% $CO_2$ for 4 hours, then centrifuging it at 1200 rpm*5 minutes, washing it with PBS three times, and collecting the cells;

(2) dispersing the collected cells in step (1) into physiological saline at a density of $5.0\times10^7$ cells/mL, and performing an ultrasonic treatment on the collected cells for 3 seconds with a gap of 1 second under conditions of 2-8° C., 25 kHz, and 360 W for 2 minutes to prepare a cell lysis solution;

(3) centrifuging the cell lysis solution prepared in step (2) at 7000 rpm*20 minutes, and filtering the obtained solution through 0.45 μm and 0.22 μm filter membranes sequentially to obtain the desired solution.

Example 10 Preparation of Freeze-Dried Cell Protein Extract Preparation of the Present Disclosure Adding dextran to the cell protein extract prepared in Example 9, stirring well, mixing well, and freezing dry. The resulting freeze-dried preparation contained 1% dextran (m/m).

Example 11 Preparation of Cell Protein Extract of the Present Disclosure

The preparation method of the cell protein extract of the present disclosure included the following steps:

(1) Adding mesenchymal passage cells with a density of $1.0\times10^7$ cells/mL to the culture medium containing DMEM/F12 45%, RPMI1640 45%, bovine serum albumin (BSA) 0.5%, epidermal growth factor (EGF) 10 μg/mL, fibroblast growth factor (FGF) 10 μg/mL, insulin transferrin 10 μg/mL, compound amino acids (18AA) 0.05% and compound 15 with 8 μmol/L; then incubating it at 37° C. and 5% $CO_2$ for 12 hours, then centrifuging it at 1200 rpm*5 minutes, washing it with PBS three times, and collecting the cells;

(2) dispersing the collected cells in step (1) into physiological saline at a density of $5.0\times10^7$ cells/mL, and performing an ultrasonic treatment on the collected cells for 3 seconds with a gap of 1 second under conditions of 2-8° C., 25 kHz, and 360 W for 2 minutes to prepare a cell lysis solution;

(3) centrifuging the cell lysis solution prepared in step (2) at 7000 rpm*20 minutes, and filtering the obtained solution through 0.45 μm and 0.22 μm filter membranes sequentially to obtain the desired solution.

Example 12 Preparation of Freeze-Dried Cell Protein Extract Preparation of the Present Disclosure Adding dextran to the cell protein extract prepared in Example 11, stirring well, mixing well, and freezing dry. The resulting freeze-dried preparation contained 2% dextran (m/m).

Experimental Example 1: Study on the Repair Effect of Cell Protein Extracts of the Disclosure on Oxidative Damaged Skin 3D skin model: EpiKutis®, purchased from EpiKutis.

SLS working solution: Weighing 0.0080 g of SLS and dissolving it in a 2 mLPBS solution. After filtration at 0.22 μm, preparing a 0.4% SLS mother solution. Taking 0.5 mL of 0.4% SLS mother solution, add 0.5 mL of PBS, and preparing it into a 0.2% SLS working solution.

WY14643 working solution: Weighing 10 mg of WY14643 (PPARα Agonist) and dissolving it in 1 mLDMSO to preparing a 30 mM WY14643 mother solution. Then adding 10 μL of WY14643 mother solution (30 mM) to a 6 mL of model culture medium and prepare it into a 50 μM of WY14643 working solution.

Model culture medium: DMEM basic culture medium.

Adding 0.9 mL of model culture medium to the 6-well plate, transferring the 3D skin model to the 6-well plate, and labeling the test number.

Blank control (BC): The skin model was left untreated and incubated in a $CO_2$ incubator (37° C., 5% $CO_2$) for 48 hours;

Negative control (NC): Adding 25 μL of 0.2% SLS working solution to the surface of the skin model, Incubating it in a $CO_2$ incubator (37° C., 5% $CO_2$) for 24 hours;

Positive control (PC): Adding 25 μL of 0.2% SLS working solution to the surface of the skin model, incubating it in a $CO_2$ incubator (37° C., 5% $CO_2$) for 24 hours; and then adding 25 μL of 50 μM WY14643 working solution, incubating it in a $CO_2$ incubator (37° C., 5% $CO_2$) for 24 hours again;

Experimental group: Adding 25 μL of 0.2% SLS working solution to the surface of the skin model, incubating it in a $CO_2$ incubator (37° C., 5% $CO_2$) for 24 hours; then adding 25 μL of 1% cell protein extract solution (freeze-dried cell protein extract powder in Example 2 was prepared into a 1% solution with physiological saline), and then incubating it in a $CO_2$ incubator (37° C., 5% $CO_2$) for 24 hours.

After 48 hours of incubation, washing and removing residual liquid inside and outside of the skin model with PBS solution. After 24 hours of fixation with 4% paraformaldehyde, loop cutting the model and observing after H&E staining. The results were shown in FIG. 1. The protein extract of the present disclosure had a significant repairing effect on oxidative damaged skin.

Experimental Example 2: Study on the Repair Effect of Cell Protein Extracts of the Disclosure on UVB Radiation Damaged Skin 3D skin model: EpiKutis®, Commercially purchased from EpiKutis.

Model culture medium: DMEM basic culture medium.

VE working solution: Take 0.5 g of VE stock solution and dissolve it in 10 mL of anhydrous ethanol to prepare a 5% mother solution; Take 100 μL of 5% mother solution and dissolve it in 10 mL of model culture medium to prepare 0.05% VE working solution.

Add 0.9 mL of model culture medium to the 6-well plate, transfer the 3D skin model to the 6-well plate, and label the test number.

Blank control (BC): The skin model was left untreated and incubated in a $CO_2$ incubator (37° C., 5% $CO_2$) for 48 hours;

Negative control (NC): After irradiating the surface of the skin model with a UVB dose of 600 mJ/cm$^2$, incubate it in a $CO_2$ incubator (37° C., 5% $CO_2$) for 24 hours; add 25 μL of 0.2% SLS working solution, incubate it in a $CO_2$ incubator (37° C., 5% $CO_2$) for 24 hours;

Positive control (PC): After irradiating the surface of the skin model with a UVB dose of 600 mJ/cm$^2$, incubate it in a $CO_2$ incubator (37° C., 5% $CO_2$) for 24 hours; add 25 μL of 0.05% VE working solution, incubate it in a $CO_2$ incubator (37° C., 5% $CO_2$) for 24 hours;

Experimental group: After irradiating the surface of the skin model with a UVB dose of 600 mJ/cm$^2$, incubate it in a $CO_2$ incubator (37° C., 5% $CO_2$) for 24 hours; Add 25 μL of 1% cell protein extract solution (freeze-dried cell protein extract powder in Example 4 was prepared into a 1% solution with physiological saline), and then incubate it in a $CO_2$ incubator (37° C., 5% $CO_2$) for 24 hours.

Figure 2:
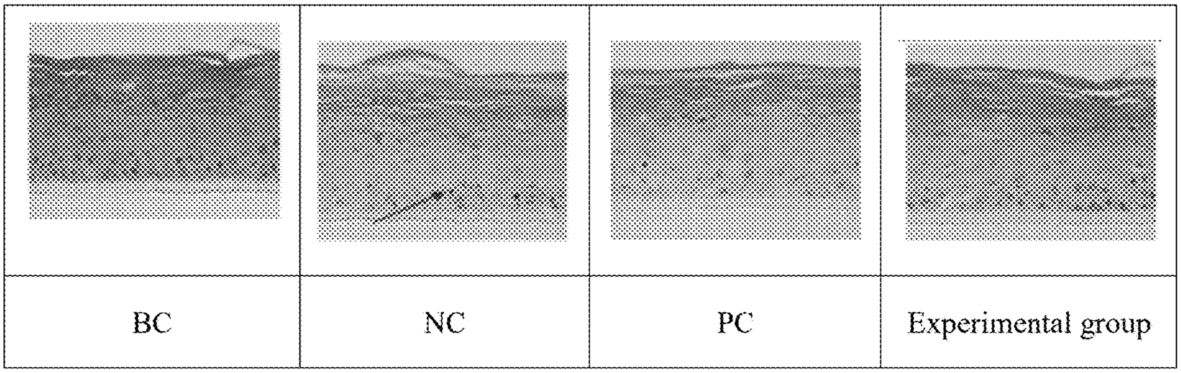
FIG. 2. Study on the repair effect of the cell protein extract of the present disclosure on skin damage caused by UVB irradiation.
Figure 3:
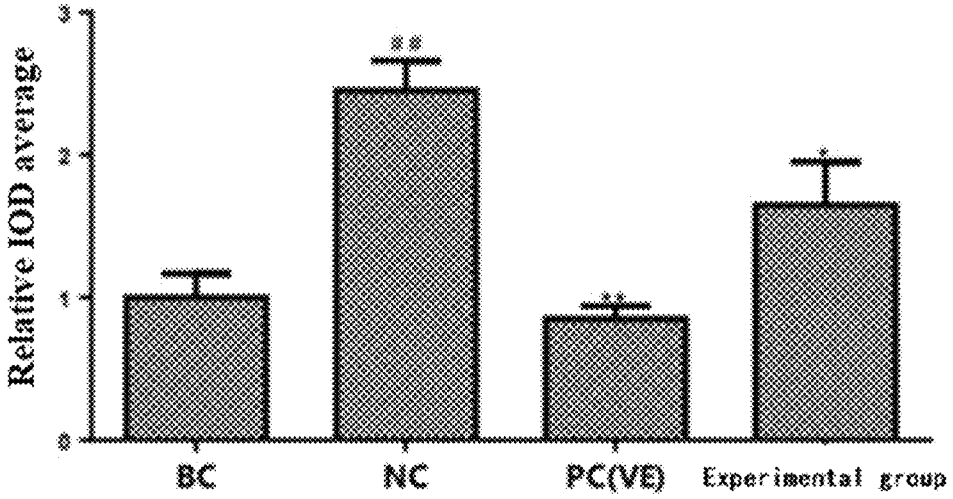
FIG. 3. The effect of the cell protein extract of the present disclosure on the generation of oxides (IOD) in skin damage caused by UVB irradiation. Mean±SD (n=3). ## indicates that compared with the blank control (BC), $p<0.01$. * indicates that compared with the NC (negative control) group, $p<0.05$, ** indicates that compared with the NC (negative control) group, $p<0.01$.
Figure 4:
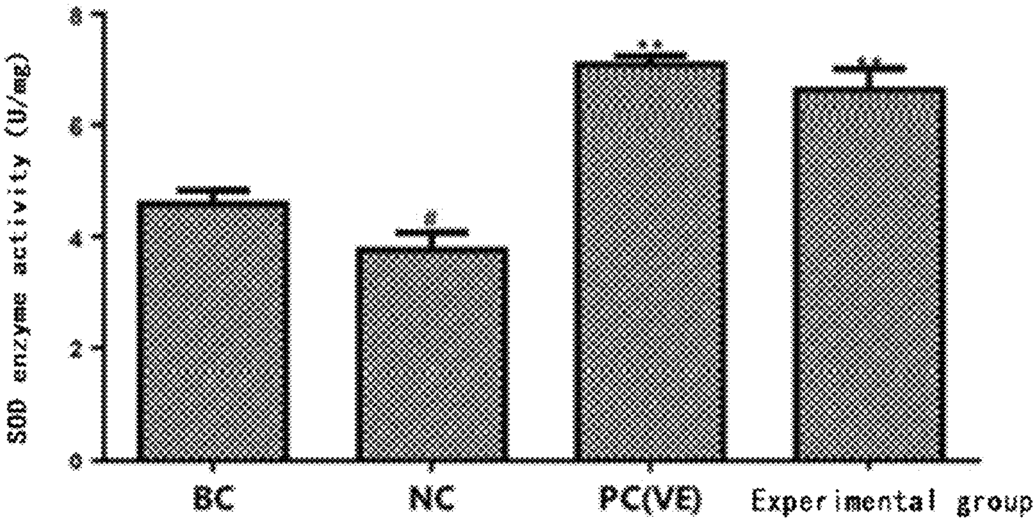
FIG. 4. The effect of the cell protein extract of the present disclosure on the generation of superoxide dismutase SOD in skin damage caused by UVB irradiation. Mean±SD (n=3). ## indicates that compared with the blank control (BC), $p<0.01$. * indicates that compared with the NC (negative control) group, $p<0.05$, ** indicates that compared with the NC (negative control) group, $p<0.01$.
Figure 5:
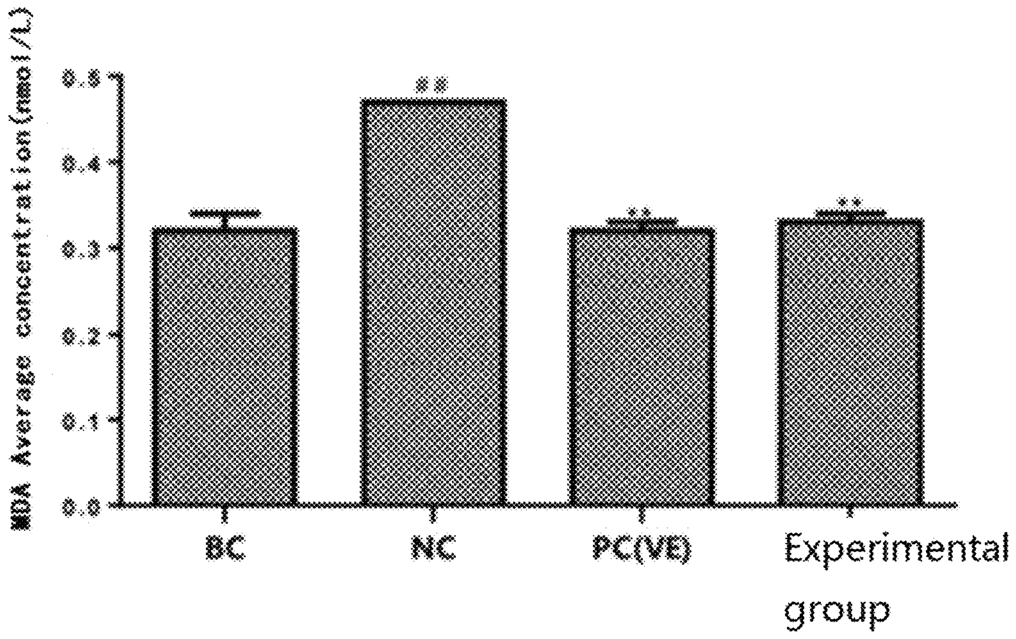
FIG. 5. The effect of the cell protein extract of the present disclosure on MDA levels in skin damage caused by UVB irradiation. Mean±SD (n=3). ## indicates that compared with the blank control (BC), $p<0.01$. * indicates that compared with the NC (negative control) group, $p<0.05$, ** indicates that compared with the NC (negative control) group, $p<0.01$.

After 48 hours of incubation, wash and remove residual liquid inside and outside of the skin model with PBS solution. After 24 hours of fixation with 4% paraformaldehyde, loop cut the model and observed after H&E staining. The results are shown in FIG. 2. Detect the levels of reactive oxygen species (IOD), superoxide dismutase, and malondialdehyde (MDA) in UVB radiation damaged skin, as shown in FIGS. 3 to 5. The cell protein extract of the present disclosure has a significant repairing effect on skin damage caused by UVB radiation.

Experimental Example 3: Study on the Repair Effect of Cell Protein Extracts of the Disclosure on Joint Injury and Cartilage Injury After general anesthesia, a 12 months old male goat weighing 47 kg was given a median incision of 8 cm on its left medial condyle. The medial edge of the patellar tendon was separated and cut open to the joint, exposing the femoral medial condyle and medial tibial plateau. The surface of the joint cartilage was smooth. A 3 mm ball drill was used to make a cartilage injury wound of 0.3*0.3*0.6 cm (length×width×depth) in the femoral medial condyle, and the incision was sutured (see FIG. 6). Taking a median incision of 8 cm on its right outer platform, separating layer by layer, and entering the joint capsule on the lateral side of the patellar tendon, exposing the femoral condyle and tibial lateral platform. The cartilage was intact and smooth. Using a 3 mm ball drill to make a cartilage injury wound of 0.6*0.3*0.3 cm (length×width×depth) on the lateral side of the platform, and suturing the incision (see FIG. 7).

Injecting 2.5 ml of freeze-dried cell protein extract solution of Example 6 into the knee joint cavity of goats unilaterally every week (preparing a 2.4% solution of freeze-dried cell protein extract solution of Example 6 with physiological saline) for three consecutive weeks. Observing every morning and evening, and the results are shown in Table 1.

TABLE 1

| | |
|---|---|
| postoperative | Slightly restricted in activities, the goat preferred to lie down rather than stand, and had a short standing time, with no abnormal diet. |
| postoperative 0 D-7 D | The goat was capable of moving but was still unwilling to stand, spent more time lying down, and had no abnormal diet or mental state. |
| postoperative 8 D-14 D | Compared to before, standing time had significantly increased, walking activities had increased, and there were no abnormalities in diet and mental health. |
| postoperative 15 D-21 D | Standing was relatively normal compared to before, with normal activity and no abnormal diet or mental state. |
| postoperative 21 D-28 D | The activity and standing were basically normal without any abnormalities, and there were no abnormalities in diet, sleep, and mental state. |
| postoperative 29 D-49 D | There were no abnormalities in activity or standing, and there were no abnormalities in diet, sleep, or mental state. |

Figure 6:
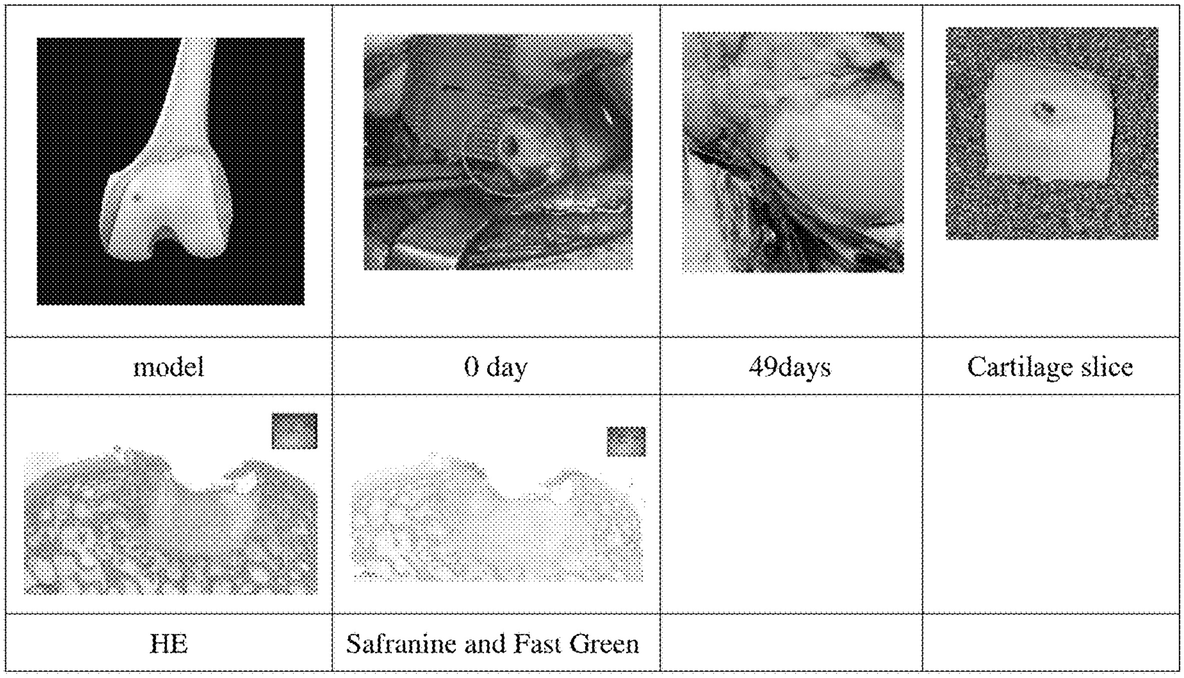
FIG. 6. Study on the repair effect of the protein extract of the present disclosure on internal condylar joint injury.
Figure 7:
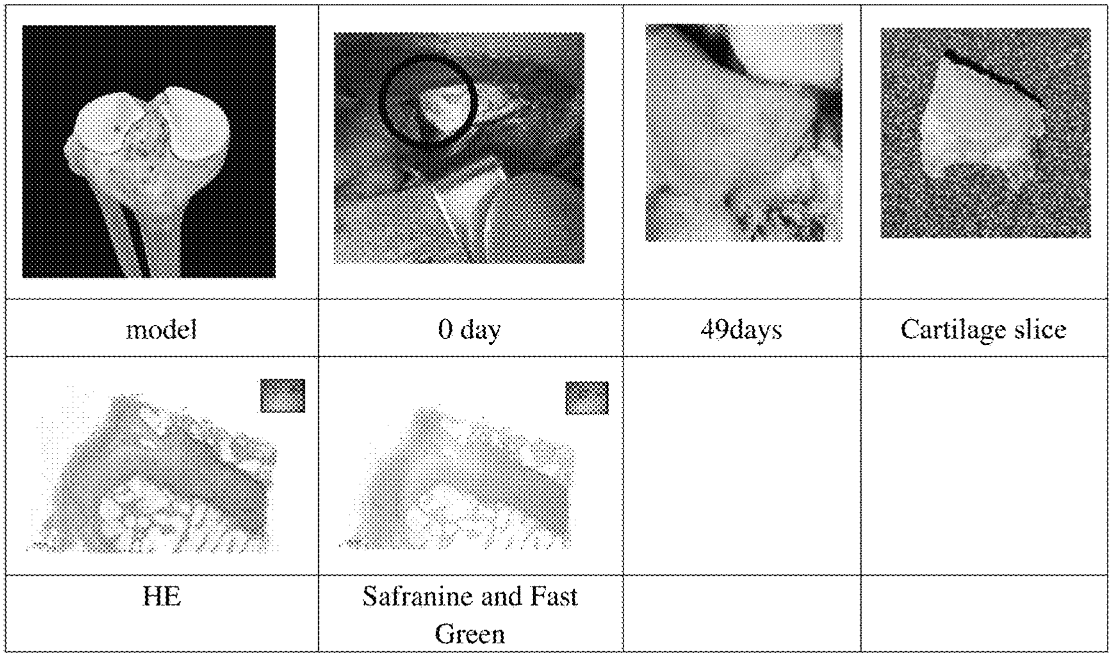
FIG. 7. Study on the repair effect of the protein extract of the present disclosure on platform joint injuries.

After 49 days of observation, the experimental sheep were anesthetized and euthanized, and cartilage sections were taken (see FIG. 6-7).

The cell protein extract of the present disclosure has a superior repairing effect on joint injuries and is safe and effective.

The above description of the specific embodiments of the present disclosure does not limit the present disclosure. Those skilled in the art may make various changes or deformations based on the present disclosure, as long as they do not deviate from the spirit of the present disclosure, they should fall within the scope of protection of the claims of the present disclosure.

What is claimed is:

1. A cell protein extract having cell repair effect, wherein the preparation thereof comprises the following steps:

(1) placing mesenchymal passage cells with a density of $1.0\times10^6$ cells/mL to $5.0\times10^7$ cells/mL in a culture medium containing DMEM/F12 40-50%, RPMI1640 40-50%, bovine serum albumin (BSA) 0.1-2%, epidermal growth factor (EGF) 1-15 μg/mL, fibroblast growth factor (FGF) 1-15 μg/mL, insulin transferrin 1-15 μg/mL, compound amino acids (18AA) 0.01-0.1%, and 2-10 μmol/L of a stressor, and then culturing the cells under conditions of 37.0° C.±0.5° C. and 5%±1.0% $CO_2$ for 10 minutes to 14 hours, and then performing isolation, washing, and collecting cells, wherein the stressor is compound 16

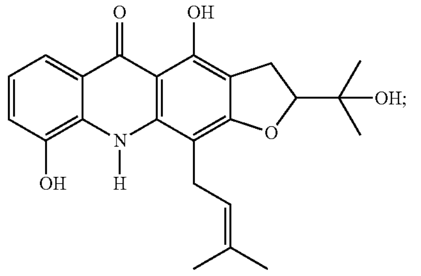 [SMILES: CC(C)=CCc1c2c(c(O)c3c(=O)c4cccc(O)c4[nH]c13)CC(C(C)(C)O)O2]

(2) dispersing the collected cells in a solvent at a density of $5.0\times10^6$ cells/mL-$1.0\times10^7$ cells/mL, and then performing an ultrasonic treatment on the collected cells at 2° C.-8° C. to prepare a cell lysate, wherein, the solvent is selected from any one or a combination of physiological saline, 5% glucose solution, phosphate buffer solution (PBS), TBPS buffer, TBST buffer, or Tris buffer;

(3) separating the cell lysate prepared in step (2), then sequentially filtering a separated solution through 0.45 μm and 0.22 μm filter membranes, thereby obtaining the cell protein extract.

2. The cell protein extract of claim 1, wherein the culture medium of step (1) contains DMEM/F12 42-45%, RPM I1640 42-45%, bovine serum protein (BSA) 0.5-1.5%, epidermal growth factor (EGF) 5-10 μg/mL, fibroblast growth factor (FGF) 5-10 μg/mL, insulin transferrin 5-10 μg/mL, compound amino acids (18AA) 0.02-0.05% and 3-8 μmol/L of the stressor.

3. The cell protein extract of claim 2, wherein the culture medium of step (1) contains DMEM/F12 45%, RPMI1640 45%, bovine serum albumin (BSA) 0.5%, epidermal growth factor (EGF) 10 μg/mL, fibroblast growth factor (FGF) 10 μg/mL, insulin transferrin 10 μg/mL, compound amino acids (18AA) 0.05%, and 4-6 μmol/L of stressors.

4. The cell protein extract of claim 1, wherein the density of mesenchymal passage cells of step (1) is $2.0\times10^6$–$2.0\times10^7$ cells/mL.

5. The cell protein extract of claim 4, wherein the density of mesenchymal passage cells of step (1) is $5.0\times10^6$–$1.0\times10^7$ cells/mL.

6. A cell repair composition consisting of a cell protein extract having cell repair effect of claim 1 and a pharmaceutically acceptable carrier.

7. A method of using the cell repair composition of claim 6, the method comprising incorporating the cell repair composition into a medication or product that is a cell repair, joint repair, cartilage repair, repair of organ damage, anti-Crohn's disease, anti-sub health, or anti-aging medication or product.

8. The cell repair composition of claim 6, wherein the cell repair composition is selected from any kind of freeze-dried preparation, gel, nasal spray, paste, cream, emulsion, liquid dressing, injection and suppository.

9. The cell repair composition of claim 6, wherein the administration method of the cell repair composition is selected from any one or a combination of application, rolling needle, microneedle, massage, intravenous injection, muscle injection, subcutaneous injection, acupoint injection or lumbar puncture.

10. The cell repair composition of claim 6, wherein the cell repair composition is capable of being incorporated into a medication or product that is cell repair of skin injury, cell repair of nerve damage, repair of pulmonary fibrosis, repair of liver damage, repair of kidney damage, ovarian repair medication or product.

11. A method of using the cell protein extract having cell repair effect of claim 1, the method comprising incorporating the cell protein extract into a medication or product that is a cell repair, joint repair, cartilage repair, repair of organ damage, anti-Crohn's disease, anti-sub health, or anti-aging medication or product.

12. The cell protein extract of claim 1, wherein the mesenchymal passage cells in step (1) are cultured in a culture medium for 30 minutes to 13 hours.

13. The cell protein extract of claim 12, wherein the mesenchymal passage cells in step (1) are cultured in a culture medium for 45 minutes to 12 hours.

14. The cell protein extract of claim 1, wherein the separation in step (3) is selected from 2000-8000 rpm*10-30 min centrifugation, multi-stage centrifugation, multi-stage filtration or a combination thereof.

15. The cell protein extract of claim 14, wherein the multi-stage centrifugation in step (3) is sequentially 3000-4000 rpm*3-5 minutes, 5000-6000 rpm*3-5 minutes, and 7000 rpm*5-8 minutes.

16. The cell protein extract of claim 14, wherein the pore size of the multi-stage filtration membrane is selected from any one of 80 μm, 50 μm, 30 μm, 10 μm, or 5 μm.

17. A method of using compound 14, the method comprising inducing stress induced stem cell to produce functional proteins with repair effects, wherein compound 16 is the following compound:

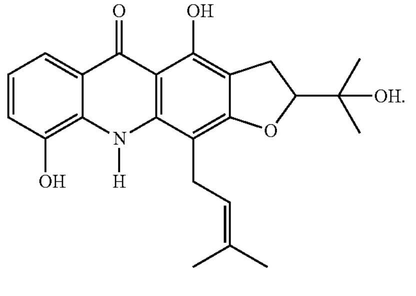 [SMILES: CC(C)=CCc1c2c(c(O)c3c(=O)c4cccc(O)c4[nH]c13)CC(C(C)(C)O)O2]

18. The method of claim 17, wherein the repair is any one of cell repair, hair follicle repair, joint repair, or nerve repair.

19. The cell protein extract of claim 1, wherein the protein extract prepared in step (3) is frozen.

20. The cell protein extract of claim 1, wherein the cell protein extract is capable of being incorporated into a medication or product that is cell repair of skin injury, cell repair of nerve damage, repair of pulmonary fibrosis, repair of liver damage, repair of kidney damage, ovarian repair medication or product.

* * * * *